(12) United States Patent
Franklin et al.

(10) Patent No.: US 7,442,188 B2
(45) Date of Patent: Oct. 28, 2008

(54) ELASTIC COMPOSITES FOR GARMENTS

(75) Inventors: Kent A. Franklin, Appleton, WI (US);
Valerie V. Finch, Neenah, WI (US);
Robin K. Nason, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1037 days.

(21) Appl. No.: 10/304,239

(22) Filed: Nov. 26, 2002

(65) Prior Publication Data

US 2003/0120246 A1 Jun. 26, 2003

Related U.S. Application Data

(63) Continuation-in-part of application No. 10/029,375, filed on Dec. 20, 2001, now Pat. No. 6,890,630.

(51) Int. Cl.
*A61F 13/20* (2006.01)
(52) U.S. Cl. .............. 604/385.23; 604/385.24; 604/385.25; 604/385.26; 604/385.27; 604/385.28; 604/385.01; 604/358; 604/384; 428/109; 428/111; 442/184; 442/329
(58) Field of Classification Search ............ 604/385.23, 604/385.24, 385.25, 385.26, 385.27, 385.28, 604/385.01, 358, 384; 428/109, 111; 442/184, 442/329, 306, 335
See application file for complete search history.

(56) References Cited

U.S. PATENT DOCUMENTS

| | | | |
|---|---|---|---|
| 4,371,417 A | 2/1983 | Frick et al. | |
| 4,729,131 A | 3/1988 | Thygesen | |
| 4,862,523 A | 9/1989 | Lipov | |
| 4,977,011 A | 12/1990 | Smith | |
| 5,092,861 A | 3/1992 | Nomura et al. | |
| 5,147,487 A | 9/1992 | Nomura et al. | |
| 5,171,388 A | 12/1992 | Hoffman et al. | |
| 5,209,801 A | 5/1993 | Smith | |
| 5,213,645 A | 5/1993 | Nomura et al. | |
| 5,221,390 A | 6/1993 | Persson et al. | |
| 5,330,598 A | 7/1994 | Erdman et al. | |
| 5,340,424 A | 8/1994 | Matsushita | |
| 5,342,341 A | 8/1994 | Igaue et al. | |
| 5,389,173 A | 2/1995 | Merkatoris et al. | |
| 5,413,654 A | 5/1995 | Igaue et al. | |
| 5,415,649 A | 5/1995 | Watanabe et al. | |
| 5,440,764 A | 8/1995 | Matsushita | |
| 5,447,508 A | 9/1995 | Numano et al. | |
| 5,449,353 A | 9/1995 | Watanabe et al. | |
| 5,500,075 A | 3/1996 | Herrmann | |
| 5,517,832 A | 5/1996 | Kristensen | |
| 5,525,175 A | 6/1996 | Blenke et al. | |
| 5,531,850 A | 7/1996 | Herrmann | |
| 5,569,227 A | 10/1996 | Vandemoortele et al. | |
| 5,576,091 A | 11/1996 | Zajaczkowski et al. | |
| 5,634,917 A | 6/1997 | Fujioka et al. | |
| 5,643,396 A | 7/1997 | Rajala et al. | |
| 5,660,664 A | 8/1997 | Herrmann | |
| 5,749,865 A | 5/1998 | Yamamoto et al. | |
| 5,766,411 A | 6/1998 | Wilson | |
| 5,779,689 A | 7/1998 | Pfeifer et al. | |
| 5,814,036 A | 9/1998 | Rönnberg et al. | |
| 5,830,203 A | 11/1998 | Suzuki et al. | |
| 5,836,931 A | 11/1998 | Toyoda et al. | |
| 5,855,573 A | 1/1999 | Johansson | |
| 5,985,070 A | 11/1999 | Boberg | |
| 6,013,065 A | 1/2000 | Suzuki et al. | |
| 6,077,254 A | 6/2000 | Silwanowicz et al. | |
| 6,129,720 A * | 10/2000 | Blenke et al. | 604/385.16 |
| 6,179,946 B1 | 1/2001 | Ward et al. | |
| 6,197,012 B1 * | 3/2001 | Mishima et al. | 604/385.04 |
| 6,197,406 B1 | 3/2001 | Kwok | |
| 6,210,387 B1 | 4/2001 | Rudberg et al. | |

(Continued)

FOREIGN PATENT DOCUMENTS

DE 3423644 A1 2/1986

(Continued)

OTHER PUBLICATIONS

International Search Report for PCT/US 02/41454 dated Jul. 17, 2003 (6 pages).

(Continued)

*Primary Examiner*—Tatyana Zalukaeva
(74) *Attorney, Agent, or Firm*—Armstrong Teasdale, LLP

(57) ABSTRACT

An elongate elastic member is secured to a substrate to form an elastic composite. The elastic member extends along an elastic axis between a first location on the substrate and a second location on the substrate spaced longitudinally from the first location. At least a portion of the elastic axis is generally non-parallel to the longitudinal axis of the substrate. The elastic member crosses its elastic axis at least twice as it extends along the elastic axis, with the elastic member crossing itself at least once as it extends along the elastic axis. In another embodiment, the elastic member generally forms a wave pattern which defines a width of the securement path and has at least two different periods along the securement path. In yet another embodiment, the elastic member defines a continuous series of loops wherein each loop defines a closed portion having a generally tear-drop shape.

5 Claims, 15 Drawing Sheets

U.S. PATENT DOCUMENTS

| | | | |
|---|---|---|---|
| RE37,154 E | 5/2001 | Nomura et al. | |
| 6,468,630 B1 | 10/2002 | Mishima et al. | |
| 6,475,600 B1 | 11/2002 | Morman et al. | |
| 6,585,841 B1 | 7/2003 | Popp et al. | |
| 6,608,236 B1 | 8/2003 | Burnes et al. | |
| 6,648,630 B2 * | 11/2003 | Tse | 431/153 |

FOREIGN PATENT DOCUMENTS

| | | |
|---|---|---|
| EP | 0 172 037 B1 | 2/1986 |
| EP | 0 626 160 B1 | 11/1994 |
| EP | 0 626 161 B1 | 11/1994 |
| EP | 0 694 297 A1 | 1/1996 |
| EP | 0 800 367 B1 | 10/1997 |
| EP | 0682509 B1 | 9/1998 |
| EP | 0787227 B1 | 6/1999 |
| JP | 06 070 958 | 3/1994 |
| JP | 07 117 125 | 5/1995 |
| JP | 11 062 805 | 3/1999 |
| WO | WO 90/04374 A1 | 5/1990 |
| WO | WO 90/09159 A1 | 8/1990 |
| WO | WO 96/18366 A1 | 6/1996 |
| WO | WO 96/23464 A1 | 8/1996 |
| WO | WO 96/23466 A1 | 8/1996 |
| WO | WO 97/00654 A1 | 1/1997 |
| WO | WO 97/06299 A1 | 2/1997 |
| WO | WO 98/25767 A1 | 6/1998 |
| WO | WO 00/37003 A2 | 6/2000 |

OTHER PUBLICATIONS

International Search Report for PCT/US 02/20723 dated Dec. 20, 2001 (5 pages).

* cited by examiner

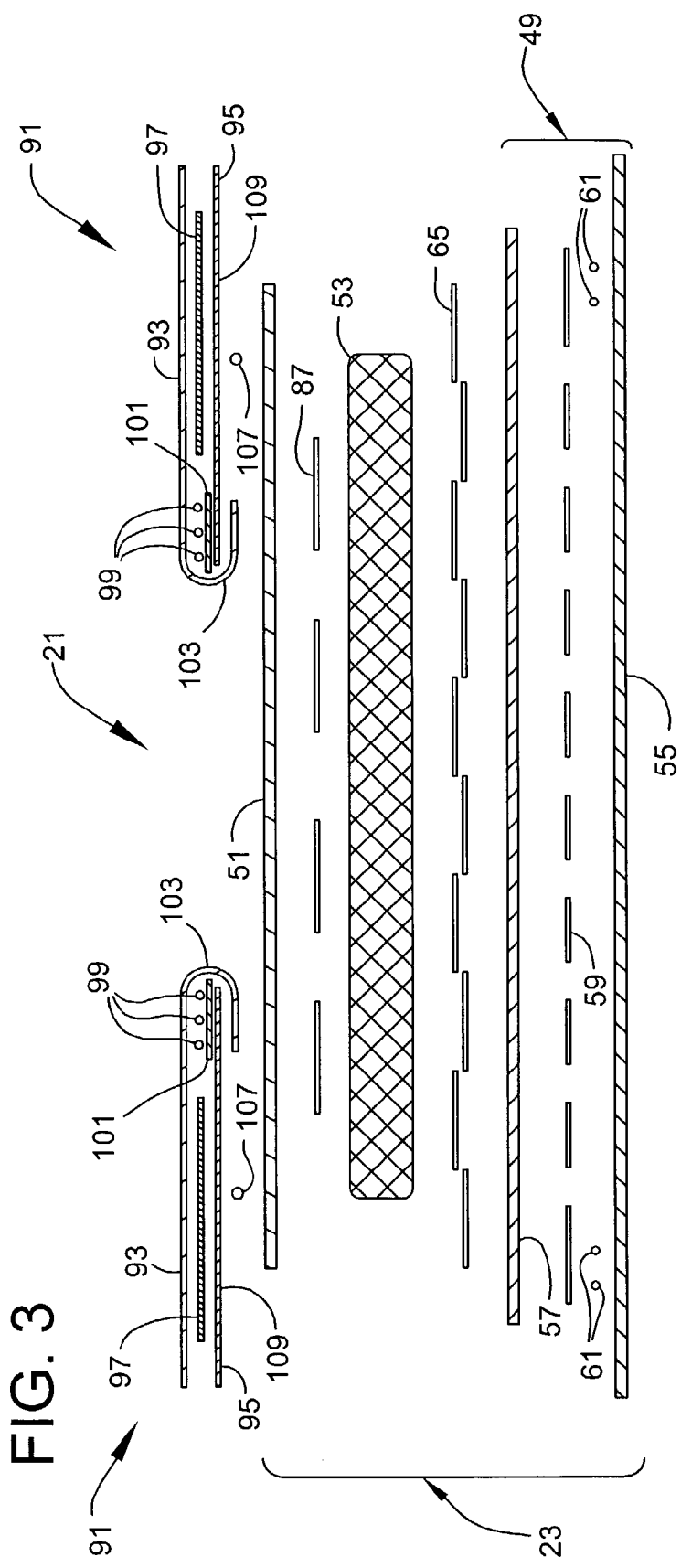

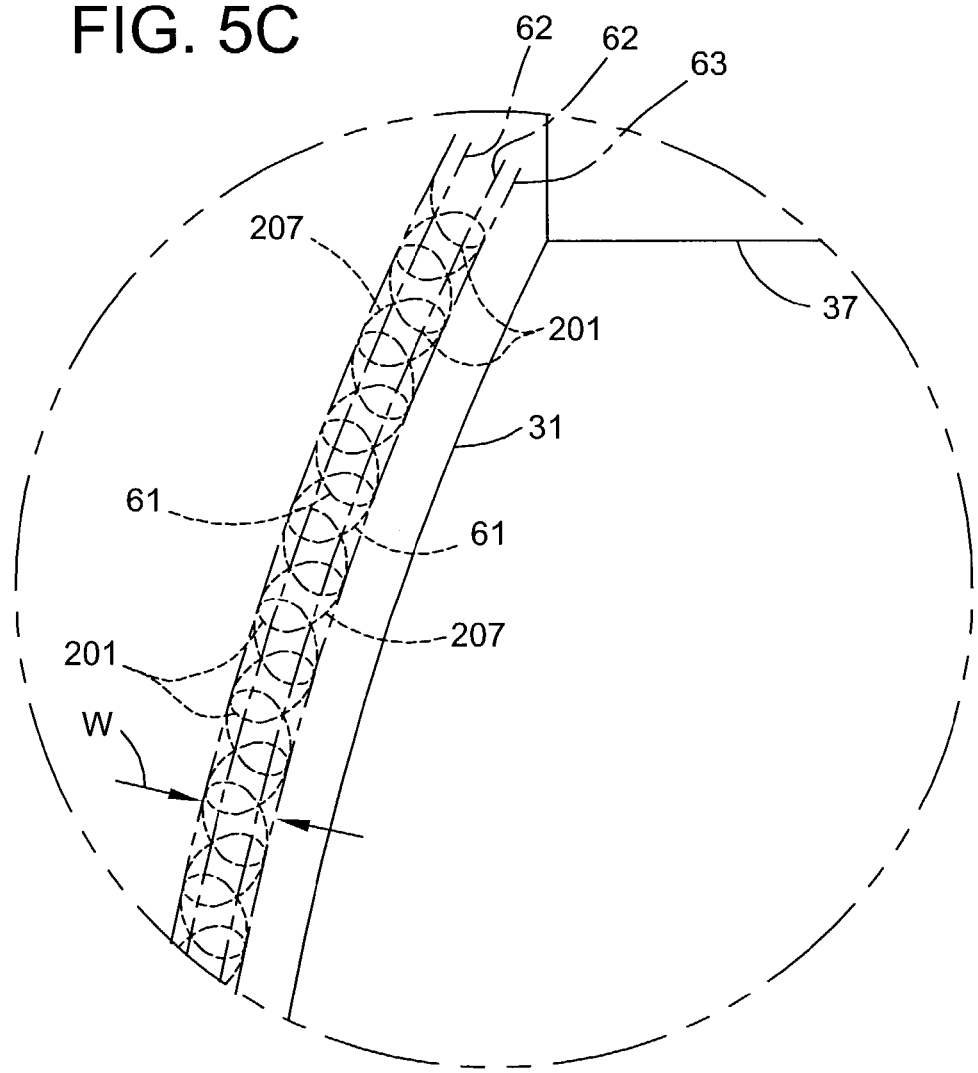

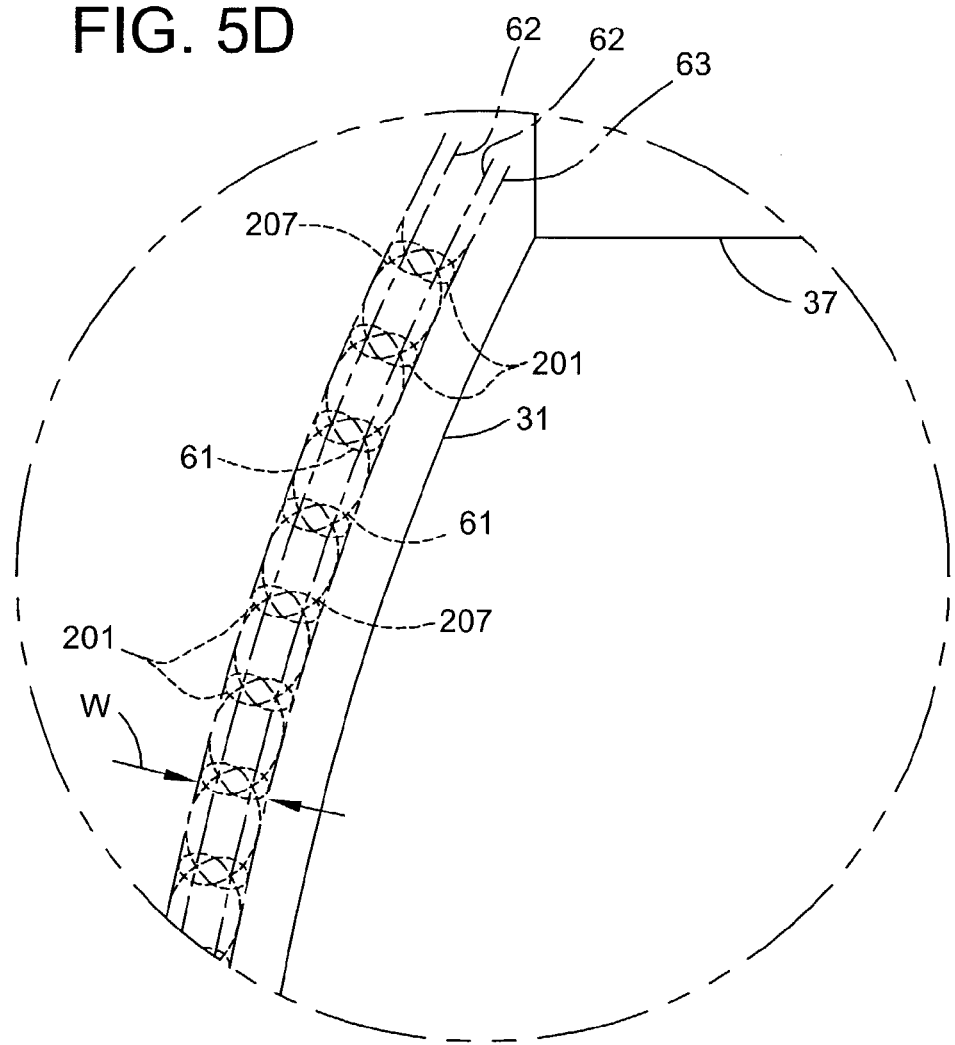

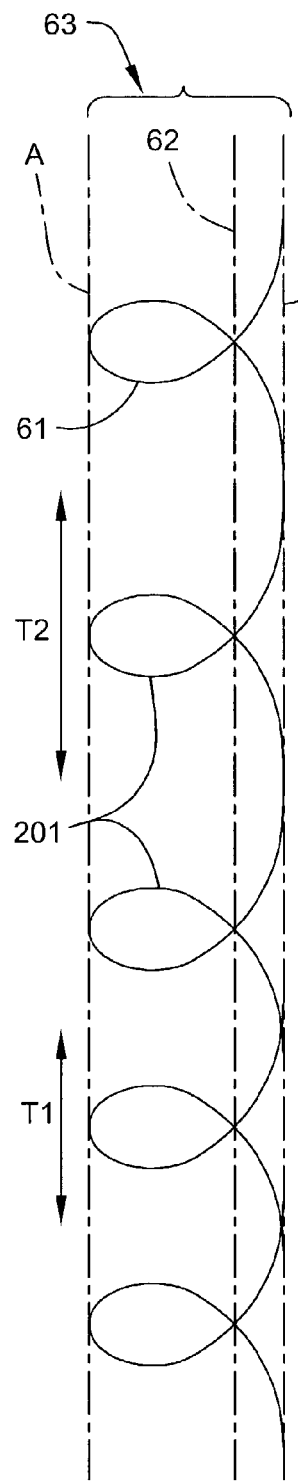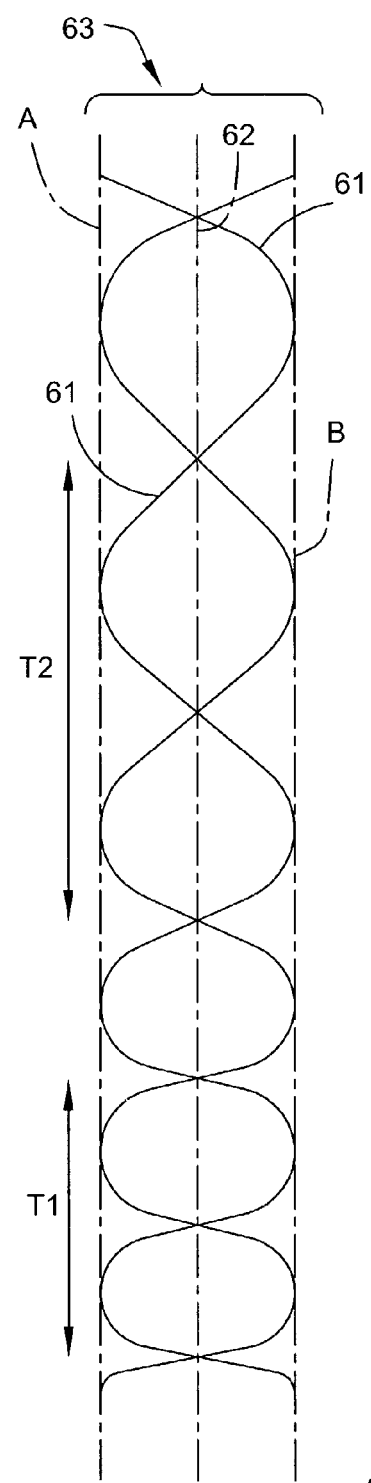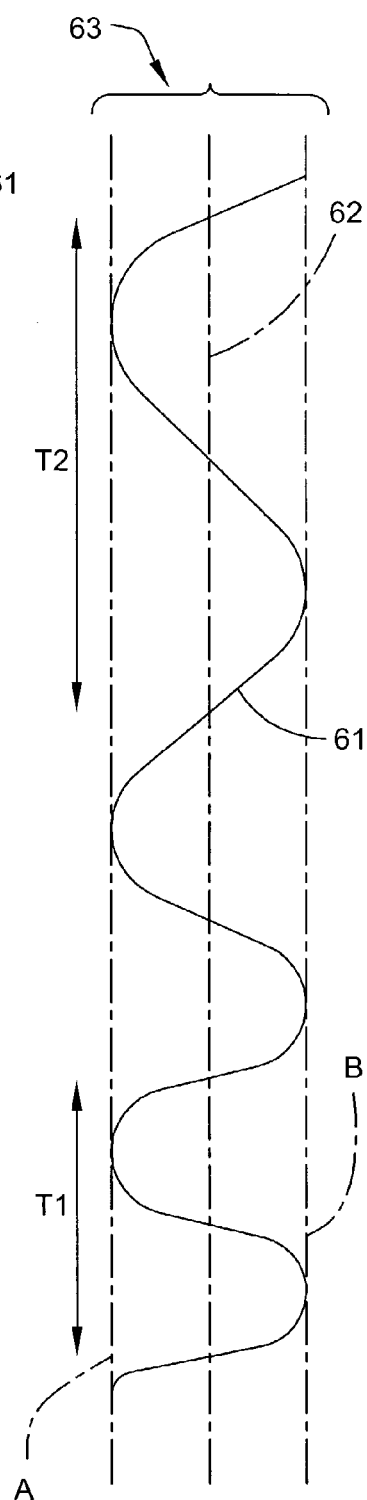

ELASTIC COMPOSITES FOR GARMENTS

CROSS-REFERENCE TO RELATED APPLICATION

This application is a continuation-in-part patent application of U.S. patent application Ser. No. 10/029,375 entitled Elastic Composites for Garments, which was filed on Dec. 20, 2001 and is fully incorporated herein by reference.

BACKGROUND OF THE INVENTION

The having elastic composites therein, and more particularly to elastic composites formed integrally with such garments, or formed separately from such garments and secured therein, to provide an elastic component to such garments.

Garments such as conventional clothing items and disposable absorbent articles often have elastic composites formed or incorporated therein which permit stretching and provide retractive forces to certain portions of the garment to provide a snug but comfortable fit for the wearer. Elastic composites also allow the garment to fit a greater range of wearer sizes. To form the elastic composite, one or more elastic members, such as strands of elastic material, are typically secured to a substrate, such as a layer of the garment material, while in a stretched condition to thereafter apply a retractive force to the substrate for gathering the substrate. The elastic composite may also be formed by securing one or more elastic members to a substrate separate from the garment, such as in the form of a strip, or ribbon. The elastic composite is then secured to the garment to incorporate the elastic composite therein.

Children's toilet training pants are one example of a garment which may incorporate elastic composites. Training pants, which serve as a disposable training aid as a child transitions from diapers to underpants, are three-dimensional articles similar to underpants in appearance but constructed with a liquid permeable inner layer and an absorbent body to provide the absorbent function of a disposable absorbent article. Elastic members in the form of elastic strands are secured within the toilet training pants at the leg openings and sometimes in other areas of the training pants such as at the waist opening and along containment flaps (if present) of the pants. The strands are adhered to a layer, or more typically between two layers, of the training pants, such as along the sides of the training pants adjacent the leg openings. The strands are typically secured within the pants while in an elongated or stretched condition (e.g., in tension) so that the retractive force of the strands gathers the pants at the leg openings to provide a snug fit around the wearer's legs.

However, despite the benefits of forming or incorporating elastic composites into garments, there continues to be a need for improvements in the formation of such elastic composites. For example, there continues to be a need for increasing the comfort of such garments against the wearer's skin and for making a more efficient use of elastic members in disposable absorbent articles to thereby decrease the cost of manufacturing such articles.

SUMMARY OF THE INVENTION

In general, one embodiment of an elastic composite comprises a substrate having a longitudinal axis. An elongate elastic member is secured to the substrate and extends along an elastic axis of the elastic member between a first location on the substrate and a second location on the substrate spaced longitudinally from the first location. At least a portion of the elastic axis is generally non-parallel to the longitudinal axis of the substrate. The elastic member crosses its elastic axis at least twice as it extends along the elastic axis, with the elastic member crossing itself at least once as it extends along the elastic axis.

In another embodiment, the elastic composite generally comprises a substrate and an elastic member secured to the substrate and extending along a securement path between a first location on the substrate and a second location on the substrate spaced longitudinally from the first location. The elastic member generally forms a wave pattern which defines a width of the securement path. The wave pattern has at least two different periods along the securement path.

In yet another embodiment, the elastic composite generally comprises a substrate and an elastic member secured to the substrate and extending along a securement path between a first location on the substrate and a second location on the substrate. The elastic member defines a continuous series of loops wherein each loop defines a closed portion having a generally tear-drop shape.

In still another embodiment, the elastic composite generally comprises a substrate having end regions and a central region extending therebetween. A first elastic member is secured to the substrate and extends along a first path defining a first wave pattern within the central region and at least one of the end regions. A second elastic member, discrete from the first elastic member, is secured to the substrate and extends along a second path in spaced relationship with the first elastic member within the central region and the at least one of the end regions. The second path defines a second wave pattern, with the spacing between the first and second paths in the at least one end region being substantially less than the spacing between the first and second paths in the central region of the substrate.

In general, one embodiment of a disposable absorbent article of the present invention has a longitudinal axis and a lateral axis and comprises a liner adapted for contiguous relationship with the wearer's skin, an outer cover, and an absorbent body between the liner and the outer cover for absorbing liquid body waste. A first elastic member is secured within the article and extends generally longitudinally along a first elastic axis. A second elastic member is secured within the article and extends generally longitudinally along a second elastic axis. The second elastic member is in generally laterally spaced relationship with the first elastic member. A third elastic member is secured within the article and extends generally longitudinally along a third elastic axis, at least a portion of which is laterally between the first and second elastic axes. The third elastic member defines a wave pattern in which the elastic member crosses the third elastic axis multiple times substantially along the entire third elastic axis.

BRIEF DESCRIPTION OF THE DRAWINGS

FIG. 3 is a separated cross-section of the training pants of FIG. 1 taken laterally through a crotch region of the pants;

FIGS. 5C, 5D, 5E and 5F are enlarged views of a portion of training pants similar to the training pants of FIG. 5 and illustrating additional patterns that may be defined by leg elastic members of the training pants;

FIGS. 6A, 6B and 6C are schematics of various additional patterns that may be defined by elastic members of the elastic composite of the present invention;

Corresponding reference characters indicate corresponding parts throughout the drawings.

DEFINITIONS

Figure 1:
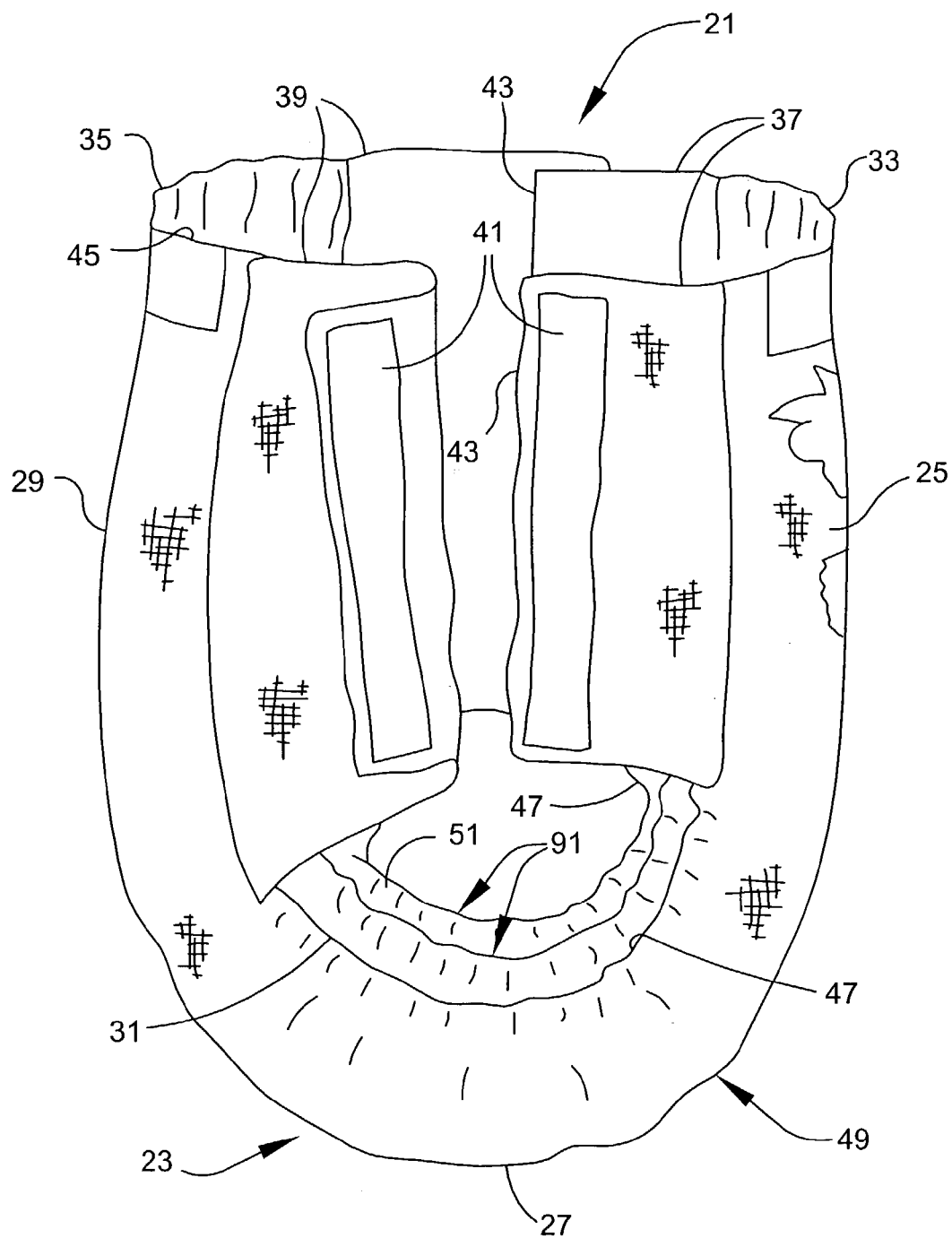
FIG. 1 is a side perspective of a child's toilet training pants.

Within the context of this specification, each term or phrase below will include the following meaning or meanings:

(a) "Bicomponent Fibers" refers to fibers that have been formed from at least two polymers extruded from separate extruders but spun together to form one fiber. Bicomponent fibers are also sometimes referred to as multicomponent or conjugate fibers. The polymers are usually, but not necessarily, different from each other. The polymers are arranged in substantially constantly positioned distinct zones across the length of the bicomponent fibers. The configuration of such a bicomponent fiber may be, for example, a sheath/core arrangement wherein one polymer is surrounded by another or may be a side-by-side arrangement, a pie arrangement or an "islands-in-the-sea" arrangement. Bicomponent fibers are taught in U.S. Pat. No. 5,108,820 to Kaneko et al.; U.S. Pat. No. 4,795,668 to Krueger et al.; U.S. Pat. No. 5,540,992 to Marcher et al.; and U.S. Pat. No. 5,336,552 to Strack et al.

(b) "Bonded" refers to the joining, adhering, connecting, attaching, or the like, of two elements. Two elements will be considered to be bonded together when they are bonded directly to one another or indirectly to one another, such as when each is directly bonded to intermediate elements.

(c) "Bonded-Carded" refers to webs that are made from fibers which are sent through a combing or carding unit, which separates or breaks apart and aligns the fibers in the machine direction to form a generally machine direction-oriented fibrous non-woven web. This material may be bonded together by methods that include point bonding, through air bonding, ultrasonic bonding, adhesive bonding or other suitable bonding technique.

(d) "Elastic, elasticized and elasticity" mean that property of a material or composite by virtue of which it tends to recover its original size and shape after removal of a force causing a deformation.

(e) "Elastomeric" refers to a material or composite which can be elongated by at least 25 percent of its relaxed length and which will recover, upon release of the applied force, at least 10 percent of its elongation. It is generally desired that the elastomeric material or composite be capable of being elongated by at least 100 percent, more preferably by at least 300 percent, of its relaxed length and recover, upon release of an applied force, at least 50 percent of its elongation.

(f) "Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

(g) "Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

(h) "Layer" when used in the singular can have the dual meaning of a single element or a plurality of elements.

(i) "Liquid impermeable" when used in describing a layer or multi-layer laminate means that liquid body waste, such as urine, will not pass through the layer or laminate, under ordinary use conditions, in a direction generally perpendicular to the plane of the layer or laminate at the point of liquid contact.

(j) "Liquid permeable" refers to any material that is not liquid impermeable.

(k) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al, which is incorporated herein by reference. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

(l) "Non-woven" and "non-woven web" refer to materials and webs of material which are formed without the aid of a textile weaving or knitting process. The web has a structure of individual fibers or threads which are interlaid, but not in an identifiable manner as in a knitted fabric. Non-woven fabrics or webs have been formed from many processes such as, for example, meltblowing processes, spunbonding processes, and bonded-carded processes.

(m) "Pliable" refers to materials which are compliant and which will readily conform to the general shape and contours of the wearer's body.

(n) "Spunbond" refers to small diameter fibers which are formed by extruding molten thermoplastic material as filaments from a plurality of fine capillaries of a spinnerette having a circular or other configuration, with the diameter of the extruded filaments then being rapidly reduced by a conventional process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No.

3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, more particularly, between about 0.6 and about 10.

(o) "Superabsorbent" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

(p) "Thermoplastic" describes a material which softens when exposed to heat and which substantially returns to a non-softened condition when cooled to room temperature.

(q) "Three dimensional" refers to a garment similar to underwear, shorts or pants in that it has continuous leg and waist openings that are bounded by material of which the garment is made. The garment may or may not have manually tearable seams.

DETAILED DESCRIPTION OF THE PREFERRED EMBODIMENTS

Referring now to the drawings and in particular to FIG. 1, an elastic composite for garments constructed in accordance with one embodiment of the present invention is shown and described herein with reference to a disposable absorbent article, and more particularly to a pair of children's toilet training pants, which is indicated in its entirety by the reference numeral 21. As used herein, a disposable absorbent article refers to an article which may be placed against or in proximity to the body (i.e., contiguous to the body) of the wearer to absorb and contain various waste discharged from the body. Such articles are intended to be discarded after a limited period of use instead of being laundered or otherwise restored for reuse.

By way of illustration only, various materials and methods for constructing training pants 21 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

Figure 2:
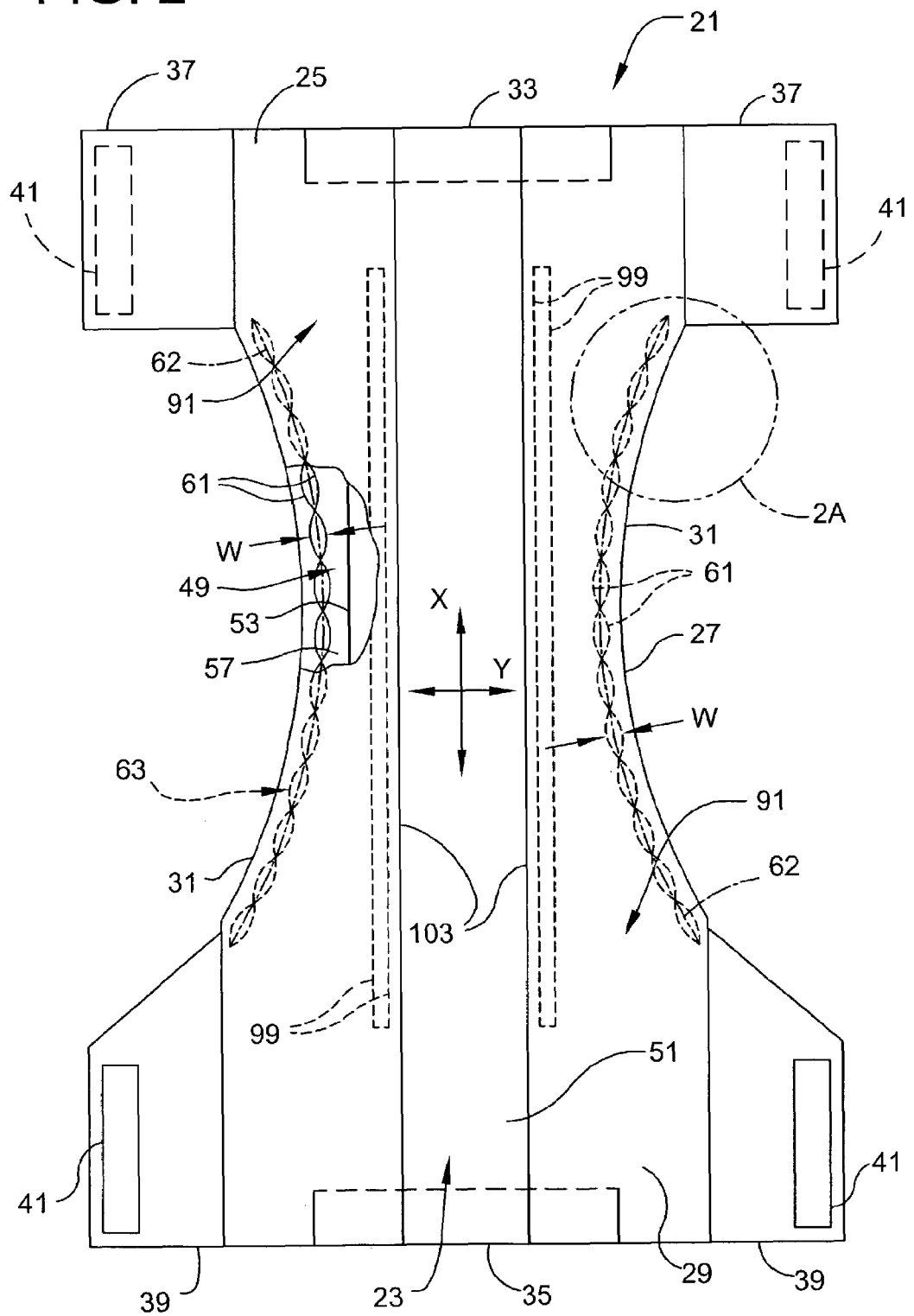
FIG. 2 is a top plan view of the training pants of FIG. 1 with the pants shown unfastened and laid flat and portions of the pants broken away to reveal an elastic composite of the present invention.

The pair of training pants 21 of the illustrated embodiment has a longitudinal axis X and a lateral axis Y as indicated in FIG. 2 and generally comprises a central absorbent assembly 23 extending longitudinally from an anterior region 25 of the training pants through a crotch region 27 to a posterior region 29 of the training pants. The central absorbent assembly 23 is generally rectangular, and is more particularly hourglass shaped, and has laterally opposite side edges 31 and longitudinally opposite front and rear waist edges or ends, respectively designated 33 and 35. As best seen in FIG. 2, the side edges 31 of the training pants 21 extend longitudinally from the anterior region through the crotch region to the posterior region for forming transversely spaced leg openings 47 (FIG. 1) of the training pants 21. Front and rear side panels 37, 39, respectively, are secured to the central absorbent assembly 23 as will be described later herein and extend laterally outward therefrom respectively at the anterior and posterior regions 25, 29 of the training pants 21.

To form the three-dimensional training pants 21 shown in FIG. 1, corresponding front and rear side panels 37, 39 (e.g., the front left side panel and the rear left side panel) are refastenably secured together, using fastening assemblies 41, along generally vertical seams 43. Alternatively, the front and rear side panels 37, 39 may be permanently secured together, such as by ultrasonic bonding, or they may be formed integrally with each other and/or with the central absorbent assembly 23. Securing the side panels 37, 39 together provides a central waist opening 45 and the transversely spaced leg openings 47 of the training pants 21. The pair of training pants 21 is worn by inserting the wearer's feet through the waist opening 45 and the respective leg openings 47; grasping the training pants near the waist opening; and then pulling the pants up along the wearer's legs until the crotch region 27 of the training pants fits snugly against the crotch of the wearer. Where the training pants 21 can be refastenably secured, the pants 21 may be worn by opening the pants flat in an unsecured configuration, fitting the pants about the wearer, and then securing the side panels together to fit the pants snugly on the wearer.

With reference to FIG. 3, the central absorbent assembly 23 of the training pants 21 comprises an outer cover, generally indicated at 49, a bodyside liner 51 and an absorbent body 53 disposed between the outer cover and the liner. The outer cover 49 can be elastic, stretchable or non-stretchable and is desirably a multi-layered laminate structure of which at least one of the layers is liquid impermeable. For example, the outer cover 49 of the illustrated embodiment is of two-layer construction, including an outer layer 55 constructed of a liquid permeable material and an inner layer 57 constructed of a liquid impermeable material joined together by a laminate adhesive 59. It is understood that the outer cover 49 may instead be constructed of a single layer of impermeable material without departing from the scope of this invention.

The liquid permeable outer layer 55 of the outer cover 49 can be any suitable material and is desirably one which provides a generally cloth-like texture. One example of such a material is a 20 gsm (grams per square meter) spunbond polypropylene non-woven web. The outer layer 55 may also be constructed of the same materials from which the bodyside liner 51 is constructed as described later herein. Also, while it is not a necessity for the outer layer 55 of the outer cover 49 to be liquid permeable, it is desired that it provide a relatively cloth-like texture to the wearer.

The liquid impermeable inner layer 57 of the outer cover 49 can be either vapor permeable (i.e., "breathable") or vapor impermeable. The inner layer 57 is desirably manufactured from a thin thermoplastic or polymeric film, although other flexible liquid impermeable materials may also be used. The liquid impermeable inner layer 57 (or the liquid impermeable outer cover 49 where the outer cover is of a single-layer construction) inhibits liquid body waste from leaking out of the pants and wetting articles, such as bed sheets and clothing, as well as the wearer and care giver.

Leg elastic members 61 are secured between the outer and inner layers 55, 57 of the outer cover 49, such as by being bonded to one or both layers by the laminate adhesive 59. Thus it will be seen that the outer and inner layers 55, 57 of the outer cover 49 each broadly define a substrate to which the elastic members 61 may be secured to broadly form an elastic composite of the present invention. It is understood that the leg elastic members 61 may be secured between the outer and inner layers 55, 57 of the outer cover 49 by adhesive (not shown) other than the laminate adhesive. It is also understood that the leg elastic members 61 may instead be secured between the outer cover 49 and the bodyside liner 51. In such a design, the leg elastic members 61 can be bonded to the outer cover 49, to the bodyside liner 51, or to both.

The elastic members 61 are desirably strands or threads of elastic material. As an example, one suitable elastic material from which the elastic members 61 may be constructed is a dry-spun coalesced multifilament elastomeric thread sold under the trade name LYCRA® and available from E. I. du Pont de Nemours and Company, Wilmington, Del., U.S.A. However, as is well known to those skilled in the art, suitable elongate elastic members 61 also include sheets, ribbons of natural rubber, synthetic rubber, or thermoplastic elastomeric polymers. The leg elastic members 61 are desirably secured between the outer and inner layers 55, 57 of the outer cover 49 while in a stretched (e.g., elastically contractible) condition such that retractive forces of the elastic members gather the training pants at the leg openings 47 to provide a snug fit around the wearer's legs. The elastic members 61 may also be colored to provide an aesthetic appearance to the pants 21.

Figure 2A:
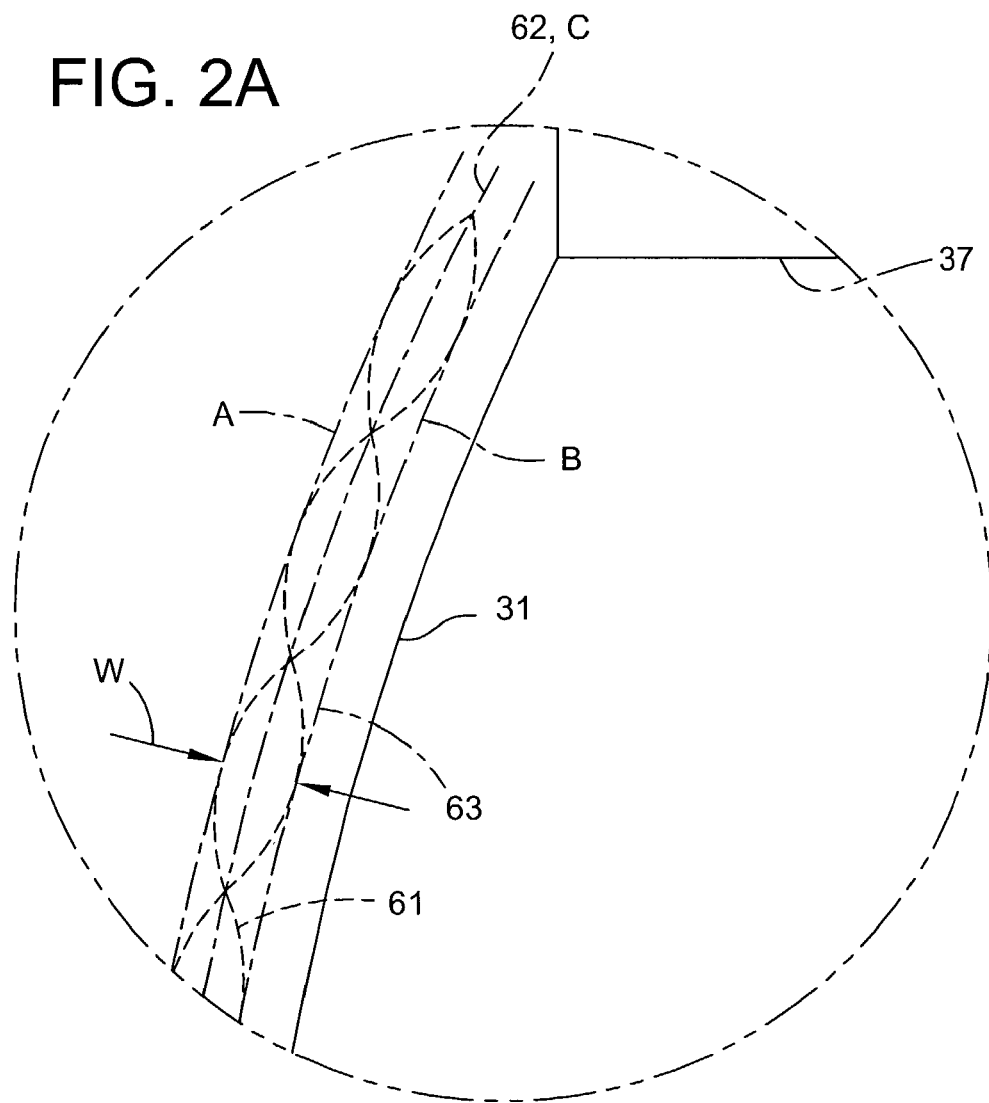
FIG. 2A is an enlarged view of a portion of the training pants of FIG. 2.

With reference to FIGS. 2 and 2A, each elastic member 61 is secured within the training pants 21 along an elastic axis 62 which extends longitudinally adjacent one of the laterally opposite side edges 31 of the training pants. As used herein, the elastic axis 62 of each elastic member 61 refers to a major or X-axis of the elastic member as it extends generally longitudinally within the training pants 21. The position of each elastic member 61 of the illustrated embodiment varies transversely relative to its respective elastic axis 62 along at least a portion thereof to define one or more securement paths 63 of the elastic members 61. However, if the position of the elastic member 61 does not vary transversely relative to its elastic axis 62, the elastic member and its elastic axis are co-linear.

Figure 4A:
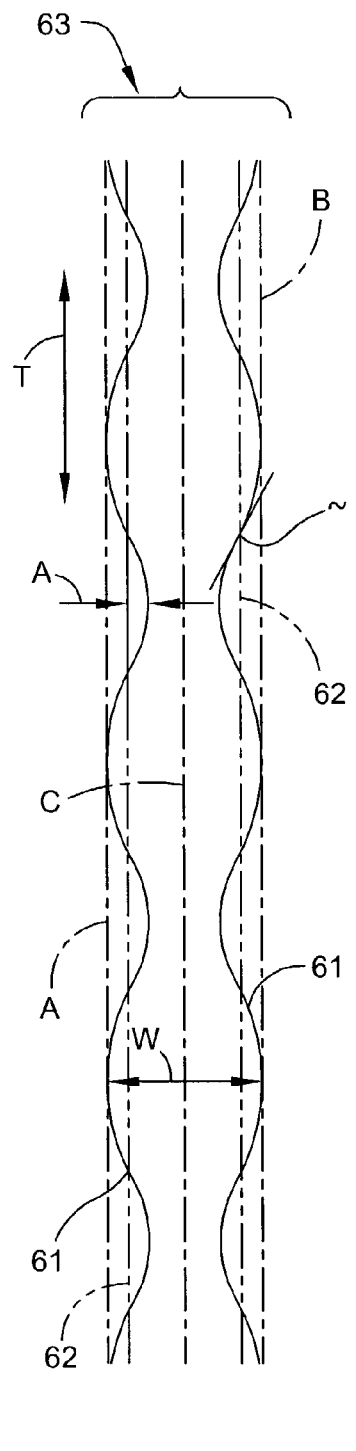
FIGS. 4A, 4B and 4C are schematics of various patterns that may be defined by elastic members of the elastic composite of the present invention.
Figure 4B:
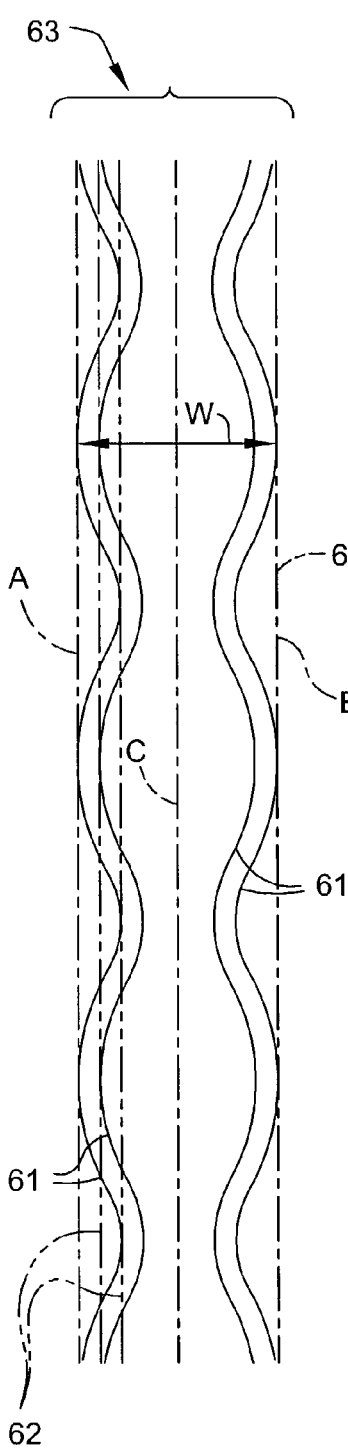
Figure 4C:
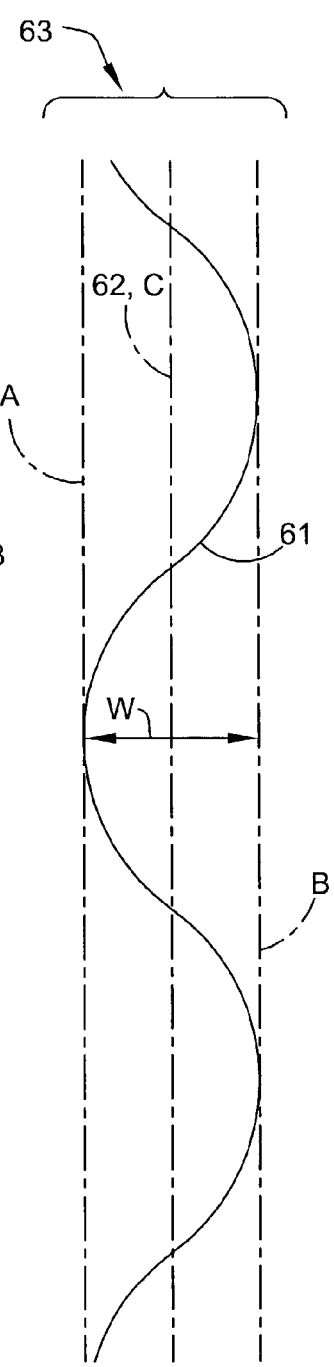

The securement path 63 as used herein refers to a path along which one or more closely spaced elastic members 61 are adhered to a substrate. For example, as seen best in FIG. 2A, the securement path 63 of the illustrated embodiment is defined by a pair of elastic members 61 and has a width W defined by edge boundaries A, B of the elastic members 61. One edge boundary A passes generally through the maxima of the elastic members 61 and the other edge boundary B passes generally through the minima of the elastic members. The elastic axes 62 of the elastic members 61 extend generally within the width W of the securement path 63, or at least on one of the edge boundaries A, B of the securement path, such that the positions of the elastic members vary transversely relative to their respective elastic axis within the securement path. In the illustrated embodiment of FIGS. 2 and 2A, the elastic axes 62 of each pair of elastic members 61 are co-linear (e.g., such that only one common elastic axis is seen in the drawings).

Where only one elastic member 61 is applied to a substrate (e.g., as shown in FIG. 4C), one edge boundary A of the securement path 63 passes generally through the maxima defined by the transverse position of the elastic member relative to the elastic axis 62 and the other edge boundary B passes generally through the minima defined by the transverse position of the elastic member relative to the elastic axis. Where the position of the elastic member 61 does not vary transversely relative to the elastic axis 62, the width W of the securement path 63 defined by a single elastic member would be substantially zero and the edge boundaries A, B of the securement path and the elastic axis of the elastic member would all be co-linear.

The elastic axes 62 and securement paths 63 defined by the elastic members 61 of the illustrated embodiment of FIG. 2 are broadly referred to herein as being crooked in that they each vary laterally as they extend longitudinally adjacent the side edges 31 of the training pants 21, e.g., generally oblique or otherwise non-parallel to the longitudinal axis X of the training pants. For example, the elastic axes 62 and securement paths 63 of the training pants 21 of FIG. 2 generally follow the contour of the side edges 31 of the training pants 21, such as in a curvilinear or arcuate path, although it is understood that the elastic axes and securement paths may not follow the contour of the side edges, and may even extend in parallel relation to the longitudinal axis X of the pants 21. As used herein, the securement path 63 is also considered to be crooked if either a centerline C extending centrally between the edge boundaries A, B, and/or either one of the edge boundaries A, B of a portion of the securement path 63 is arcuate, bent or otherwise oblique or non-parallel relative to a particular axis, such as the longitudinal axis X of the pants 21.

Each leg elastic member 61 shown in FIG. 2 generally defines a wave pattern, and more particularly a periodic wave pattern such as a sinusoidal wave pattern, along at least a portion of the respective elastic axis 62 of the elastic member. Desirably, at least one, and more desirably at least two, periods of the wave pattern are formed along the length of each elastic axis 62, e.g., in the illustrated embodiment, within the training pants 21. FIGS. 2, 4A, 4B, 4C and 5 are exemplary wave patterns that may be defined by one or more elastic members 61 as they extend within the training pants 21. For example, FIG. 4A illustrates a pair of elastic members 61 defining two periodic wave patterns along respective elastic axes 62. Each wave pattern generally has an amplitude A and a period T as the elastic member extends along its elastic axis 62.

In the illustrated embodiment, the amplitude A and period T of the periodic wave pattern formed by each elastic member 61 are such that the composite formed by the elastic member and the substrate to which it is bonded, e.g., the outer and inner layers 55, 57 of the outer cover 49, is more stretchable in the direction of the securement path 63 (e.g, generally tangential to the securement path) than in a generally transverse direction relative to the securement path. For example, a slope S defined by the change in the transverse position of each elastic member 61 relative to its elastic axis is desirably between about −1 and about 1. However, it is contemplated that the slope S may be greater than 1, or less than −1, and/or that the composite incorporating the elastic member is as stretchable, or more stretchable, in the transverse direction relative to the elastic axis without departing from the scope of this invention.

The elastic members 61 shown in FIG. 4A generally have a constant and equal amplitude A and period T, with the periodic wave pattern of one elastic member being the negative of the other (e.g., 180° out of phase therewith) so that the transverse spacing between the elastic members varies within the securement path 63. The elastic members 61 are also sufficiently spaced to avoid crossing each other within the securement path 63. The periodic wave patterns of the elastic members 61 shown in FIG. 2 also have a substantially constant and equal amplitude and period throughout the securement path 63, and the periodic wave pattern defined by one elastic member is the negative of the periodic wave pattern defined by the other elastic member. In addition, the elastic axes 62 of the elastic members 61 of FIG. 2 are sufficiently close so that the elastic members periodically cross each other along the securement path 63. FIG. 4B illustrates two pairs of elastic members 61 which together defining a securement path 63. In this embodiment, each pair of elastic members 61 defines two periodic wave patterns having a substantially constant and equal amplitude and period, with the elastic members arranged in parallel, spaced relationship with each other along the securement path 63. The periodic wave patterns of one pair of elastic members 61 are the negative of the periodic wave patterns of the other pair of elastic members. FIG. 4C illustrates a single elastic member 61 defining the securement path 63 wherein the wave pattern defined by the elastic member is a sinusoidal wave pattern.

It is contemplated that where two or more elastic members 61 define the securement path 63, the pattern defined by one elastic member 61 may have a different amplitude and/or period than the pattern defined by one or more of the other elastic members, and that the elastic members may be more closely or distantly spaced relative to each other than as shown in the illustrated embodiments, without departing from the scope of this invention. It is also understood that where the securement path 63 is defined by more than one elastic member 61, one of the elastic members (and hence the elastic axis 62 thereof) may not extend the full length of the securement path 63.

FIGS. 5, 5A, 5B, 5C, 5D, 5E, 5F, 6A, 6B and 6C illustrate additional wave patterns that may be formed by one or more elastic members 61 secured within the training pants 21. More particularly, in FIG. 5 a leg elastic member 61 extends generally longitudinally within the training pants 21 along an elastic axis 62 (FIG. 5A) adjacent each side edge 31 of the pants. The position of each elastic member 61 varies transversely relative to its respective elastic axis 62 to define a wave pattern in which the elastic member crosses itself at least once as it extends longitudinally along the elastic axis. More particularly, the wave pattern defined by each elastic member 61 is a generally continuous series of loops 201 wherein (with particular reference to FIGS. 5A and 5B) each loop comprises a closed portion, generally indicated at 203, a crossing point 205 at which the elastic member crosses itself, and an open portion, generally indicated at 207. The loops 201 are formed so that the closed portions 203 thereof extend generally transverse to the securement path 63 and in the illustrated embodiment point generally in toward the longitudinal axis X of the pants 21. However, it is understood that the wave pattern defined by the elastic member 61 may be such that the closed portions 203 of the loops 201 point generally out toward the side edges 31 of the pants 21. The securement path 63 defined by each elastic member 61 of the illustrated embodiment has a width W defined by one edge boundary A passing generally through the apex of the closed portion 203 of each loop 201 and an opposite edge boundary B passing generally through the minima of the open portion 207 of each loop.

Figure 5:
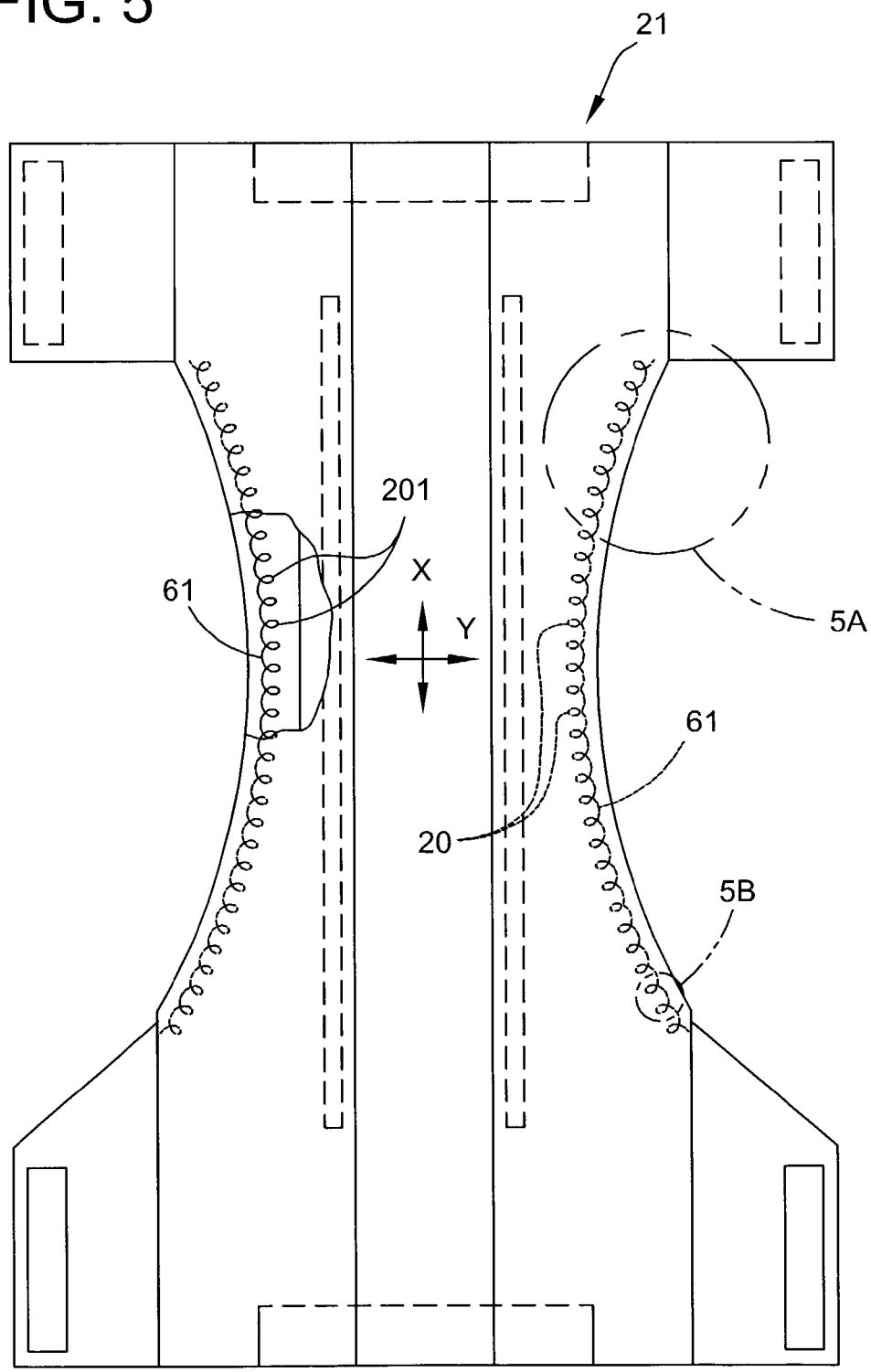
FIG. 5 is a top plan view of training pants similar to FIG. 2 and illustrating another pattern that may be defined by leg elastic members of the training pants.
Figure 5A:
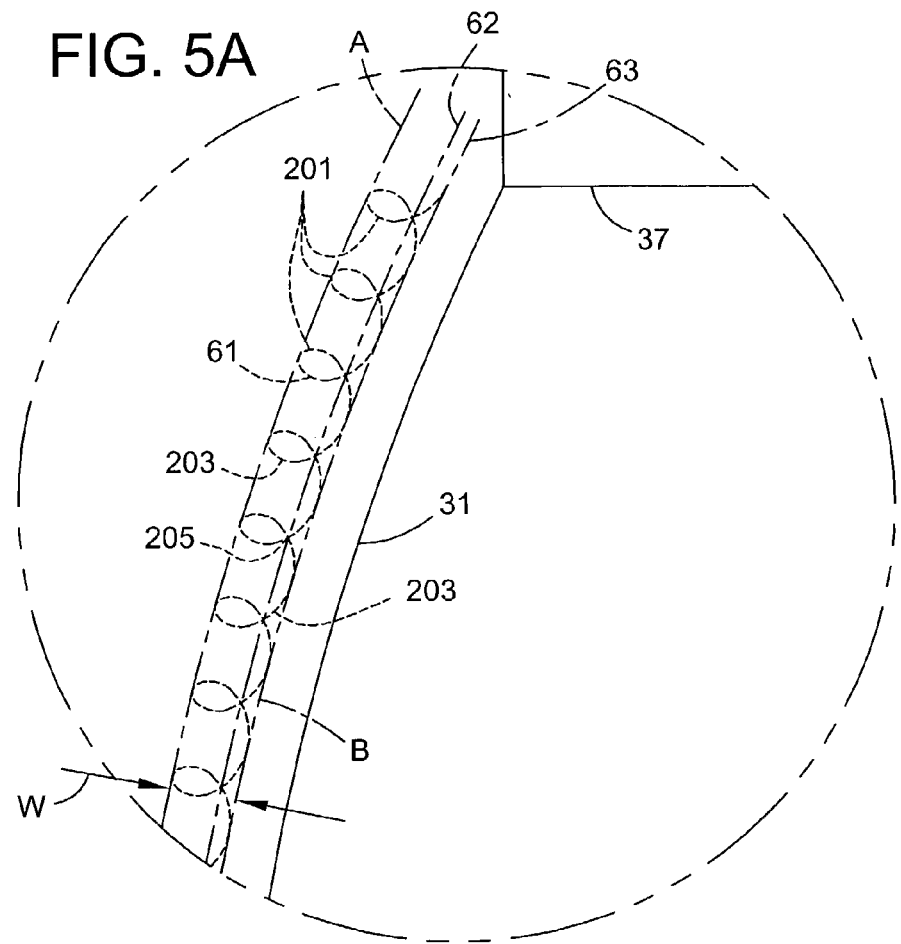
FIG. 5A is an enlarged view of a portion of the training pants of FIG. 5.
Figure 5B:
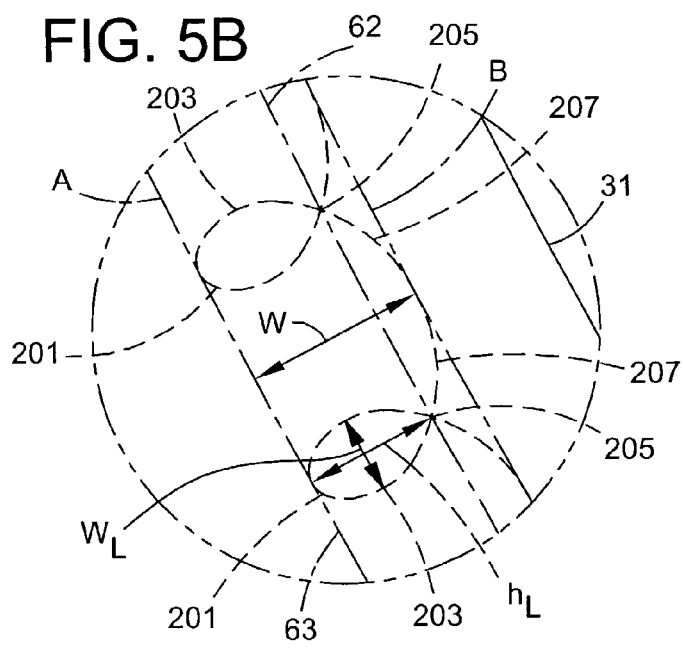
FIG. 5B is a further enlarged view of the portion of the training pants of FIG. 5A.
Figure 5E:
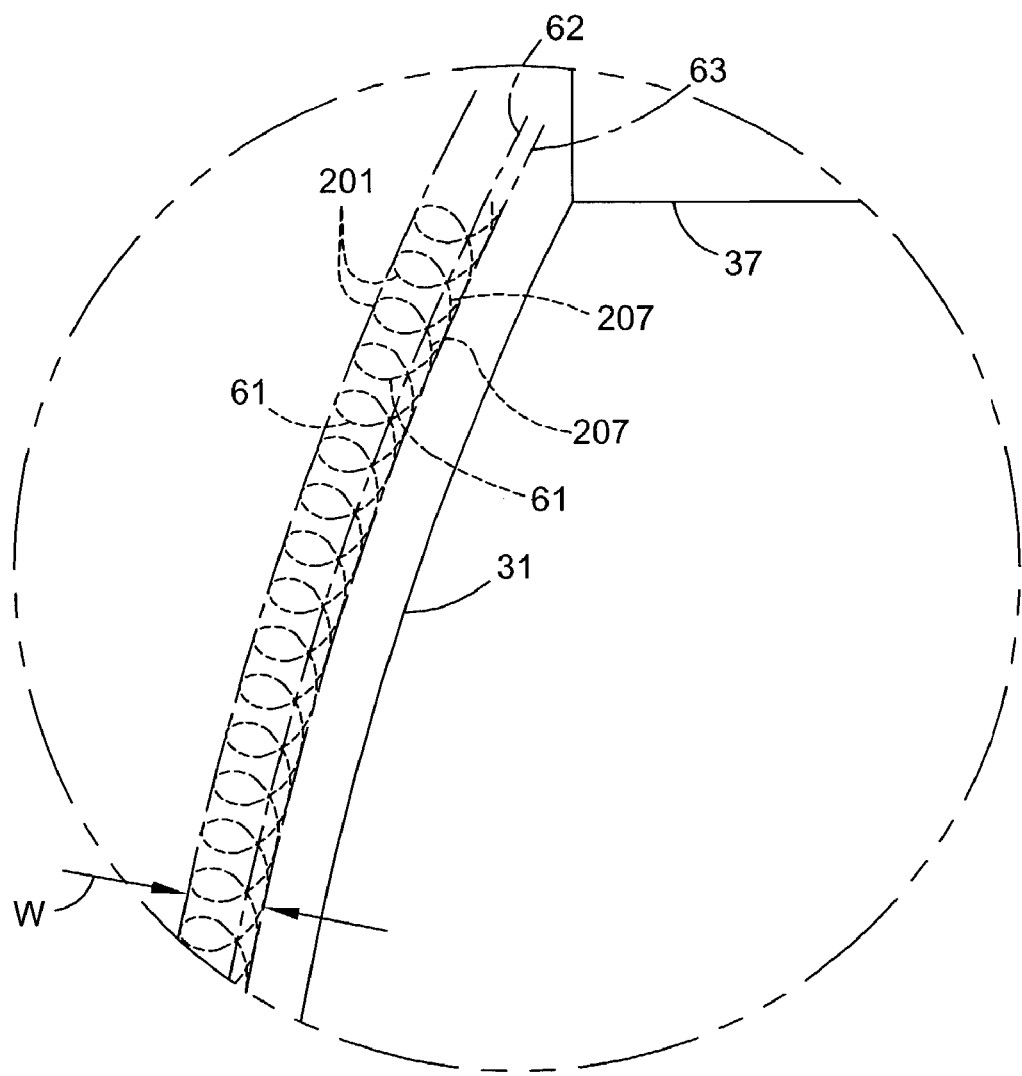

As seen best in FIG. 5B, the closed portion 203 of each loop 201 is desirably tear-drop shaped and has a height, $h_L$ measured transverse to the elastic axis generally from the crossing point 205 to the apex of the closed portion of the loop (e.g., the edge boundary A of the securement path 63), and a width $w_L$ which is substantially less than the height of the closed portion. The maximum width $w_L$ of the closed portion 203 of each loop 201 is desirably nearer to the apex of the closed portion than to the crossing point 205 of the loop. However, it is understood that the loop 201 may be other than tear-drop shaped, and that the maximum width $w_L$ of the loop may be nearer the crossing point 205 than the apex of the closed portion 203 of the loop, or it may be equidistant therebetween, without departing from the scope of this invention.

In FIG. 5C, the securement path 63 is defined by a pair of elastic members 61 wherein each elastic member defines a respective wave pattern in the form of a continuous series of loops 201. The wave pattern defined by one elastic member 61 is substantially the negative of the wave pattern defined by the other elastic member and is generally shifted relative thereto so that the loops 201 formed by one elastic member are intersticed with the loops formed by the other elastic member. Thus, the width W of the securement path 63 is defined by the respective minima of the open portions 207 of the loops 201 formed by the elastic members 61.

Figure 5F:
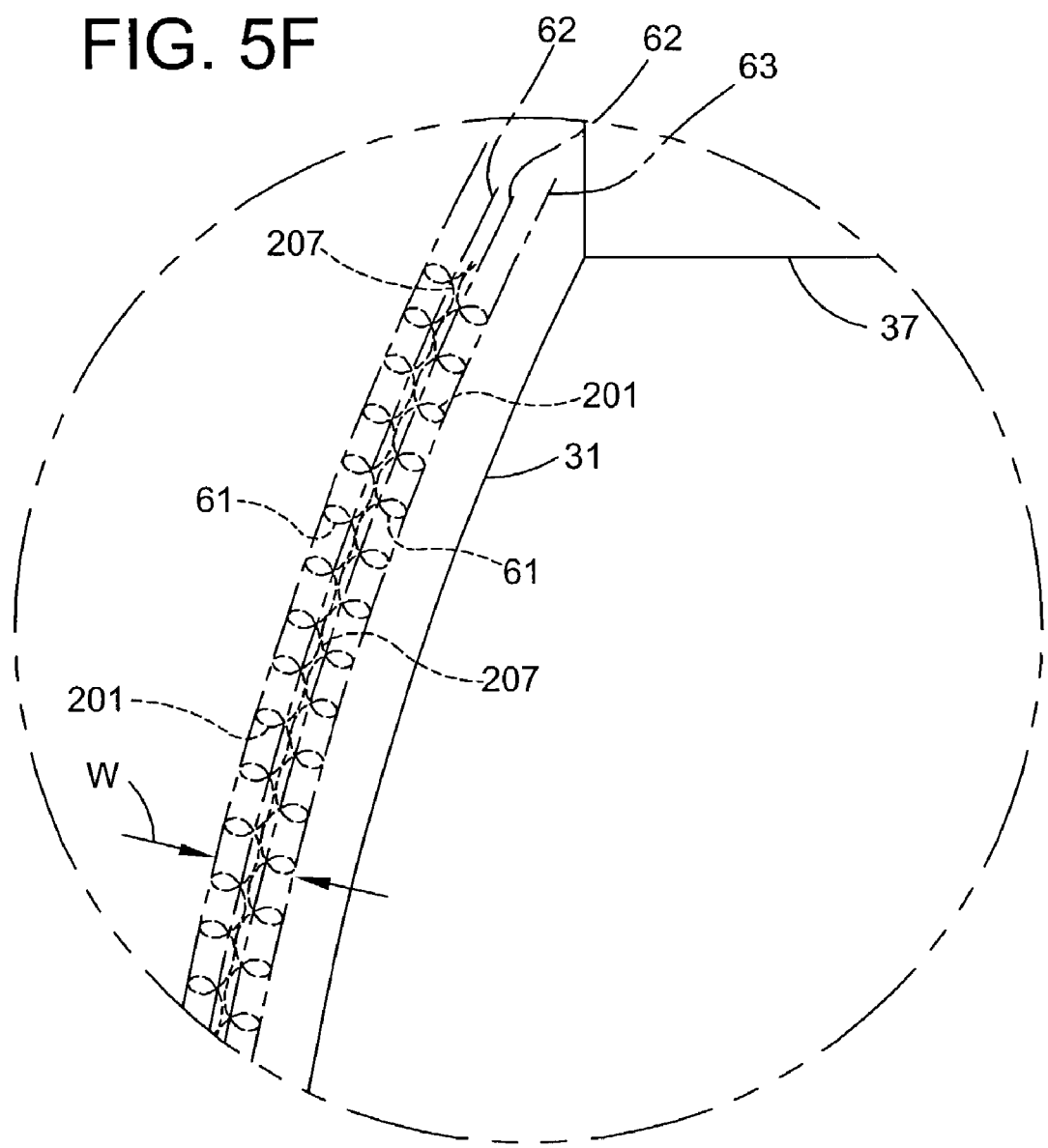

Alternatively, it is contemplated that one elastic member 61 may not be shifted relative to the other elastic member so that the closed portions 203 of the loops 201 formed by the elastic members cross each other repeatedly along the securement path 63 as shown in FIG. 5D. It is also contemplated that the closed portions 203 of the loops 201 formed by one elastic member may point in the same direction (FIG. 5E) as the closed portions of the loops formed by the other elastic member, or that the loops may point in opposite directions as shown in FIG. 5F, with the minima of the open portions 207 of the loops in closely spaced (e.g., back-to-back) relationship with each other, without departing from the scope of this invention.

FIGS. 6A, 6B and 6C illustrate additional wave patterns defined by one or more elastic members 61 in which in which each wave pattern has at least two different periods $T_1$, $T_2$ defined along different segments of the respective elastic axis 62 of each elastic member. For example, as shown in FIG. 6A, an elastic member 61 may define a wave pattern in the form of a continuous series of loops 201, with the spacing between consecutive loops being different as the elastic member extends along different segments of the elastic axis 62. The wave pattern defined by the single elastic member 61 shown in FIG. 6C is a sinusoidal wave pattern in which the period $T_1$, $T_2$ of the wave pattern is different as the elastic member extends along different segments of the elastic axis 62. FIG. 6B illustrates a pair of elastic members 61 defining respective sinusoidal wave patterns within the width W of the securement path 63. The periodic wave pattern defined by one elastic member 61 is the negative (e.g., 180° out of phase) of the periodic wave pattern defined by the other elastic member. The elastic members 61 of FIG. 6B are also sufficiently close so that the elastic members periodically cross each other along the securement path 63. Each wave pattern has different periods $T_1$, $T_2$ as the elastic members 61 extend along different segments of their respective elastic axis 62.

By securing one or more elastic members 61 between the outer and inner layers 55, 57 of the outer cover 49 in a wave pattern within the securement path 63, the elastic members affect a substantially increased surface area of the outer cover in comparison to unpatterned elastic members (e.g., which are generally parallel to or otherwise co-linear with the securement path 63). As a result, the retractive forces of the elastic members 61 act against a greater surface area of the wearer's skin (i.e., a surface area roughly equal to the width of the securement path times its length), thereby increasing comfort to the wearer and reducing the risk that the elastic members will leave indentations or marks on the wearer. Also, because the elastic members 61 are spread over a wider surface area of the outer cover 49, a lesser number of elastic members may be needed to provide the desired fit of the pants 21 against the wearer's skin. For example, a pair of elastic members 61 formed in periodic wave patterns may replace three unpatterned elastic members.

Now referring back to FIG. 3, the absorbent body 53 is somewhat rectangular and is desirably constructed to be generally compressible, pliable, non-irritating to the wearer's skin and capable of absorbing and retaining liquid body waste, such as urine. The absorbent body 53 overlays the inner layer 57 of the outer cover 49, extending laterally between the leg elastic members 61, and is secured to the inner layer, such as by being bonded thereto with adhesive 65.

The bodyside liner 51 overlays the absorbent body 53 to isolate the wearer's skin from liquid body waste retained by the absorbent body and is secured to at least a portion of the absorbent body, such as by being bonded thereto with adhesive 87. The liner 51 further extends beyond the absorbent body 53 to overlay a portion of the inner layer 57 of the outer cover 49, particularly in the crotch region 27 of the pants 21, and is secured thereto, such as by being bonded thereto by adhesive 65, to substantially enclose the absorbent body between the outer cover and the liner about the periphery of the absorbent body. Although the bodyside liner 51 shown in FIG. 3 is slightly narrower than the outer cover 49, it is understood that the liner and outer cover may be of the same dimensions, or the liner may be sized larger than the outer cover, without departing from the scope of this invention. It is also contemplated that the liner 51 may not extend beyond the absorbent body 53 and may not be secured to the outer cover 49 and/or to the absorbent body 53. The bodyside liner 51 is desirably compliant, soft feeling, and non-irritating to the wearer's skin and can be less hydrophilic than the absorbent body 53 to provide a relatively dry surface to the wearer and permit liquid body waste to readily penetrate through its thickness.

The bodyside liner 51 can be manufactured from a wide selection of web materials, such as synthetic fibers (e.g., polyester or polypropylene fibers), natural fibers (e.g., wood or cotton fibers), a combination of natural and synthetic fibers, porous foams, reticulated foams, apertured plastic films, or the like. Various woven and non-woven fabrics can be used for the bodyside liner 51. For example, the liner 51 can be composed of a meltblown or spunbonded web of polyolefin fibers. Alternatively, the liner 51 can be a bonded-carded web composed of natural and/or synthetic fibers. The bodyside liner 51 can also be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 available from Uniqema, Inc., a division of ICI of New Castle, Del., U.S.A, and GLUCOPON® 220UP available from Cognis Corporation of Ambler, Pa., U.S.A, in an active ratio of 3:1. The surfactant can be applied by any conventional means, such as spraying, printing, brush coating or the like. The surfactant can be applied to the entire liner 51 or it can be selectively applied to particular sections of the liner.

A particularly suitable bodyside liner 51 is constructed of a non-woven web having a basis weight of about 27 gsm. The non-woven web can be a spunbonded bicomponent web or a bonded-carded bicomponent web. Suitable bicomponent fibers include a polyethylene/polypropylene bicomponent fiber available from CHISSO Corporation, Osaka, Japan. In this particular bicomponent fiber, the polypropylene forms the core and the polyethylene forms the sheath of the fiber. Fibers having other orientations, such as multi-lobe, side-by-side, end-to-end may be used without departing from the scope of the invention. Also, although the outer cover 49 and bodyside liner 51 of the central absorbent assembly 23 can include elastomeric materials, it is contemplated that the central absorbent assembly may instead be generally inelastic, wherein the outer cover, the bodyside liner and the absorbent body 53 are composed of materials which are generally non-elastomeric.

The front and rear side panels 37, 39 of the training pants 21 may be bonded to the central absorbent assembly 23 at the respective anterior and posterior regions 25, 29 of the pants and extend out beyond the laterally opposite side edges 31 of the assembly. For example, the front side panels 37 of the illustrated embodiment are secured to the inner layer 57 (FIG. 3) of the outer cover 49, such as by being bonded thereto by adhesive (not shown), by thermal bonding or by ultrasonic bonding. These side panels 37 may also be secured to the outer layer 55 of the outer cover 49, such as by being bonded thereto by adhesive (not shown), by thermal bonding or by ultrasonic bonding. The rear side panels 39 are secured to the outer and inner layers 55, 57 of the outer cover 49, at the posterior region 29 of the training pants 21, in substantially the same manner as the front side panels 37. Alternatively, the side panels 37, 39 may be formed integrally with the central absorbent assembly 23, such as by being formed integrally with the outer cover 49, the bodyside liner 51 or other layers of the pants 21.

Containment flaps, generally indicated at 91, are secured to the bodyside liner 51 in generally parallel, spaced relation with each other laterally inward of the leg openings 47 to provide a barrier against the flow of urine to the leg openings. The containment flaps 91 extend longitudinally from the anterior region 25 of the training pants 21, through the crotch region 27 to the posterior region 29 of the pants. Each containment flap 91 comprises a non-woven layer 93 and a film layer 95 secured to the non-woven layer, such as by being bonded thereto by adhesive 97. Flap elastic members 99 are secured by suitable adhesive 101 between the non-woven layer 93 and the film layer 95 generally at a distal end 103 of the flap 91, with the non-woven layer 93 being folded over the flap elastic members 99 and the film layer 95 at the distal end 103. The flap 91 is secured to the bodyside liner 51 by a seam of adhesive 107 to define a proximal end 109 of the flap.

The flap elastic members 99 of the illustrated embodiment comprise three individual strands of elastomeric material extending longitudinally along the distal end 103 of the flap 91 in generally parallel, spaced relation with each other. One suitable elastic strand is a LYCRA® T151 940 decitex elastic which can be obtained from E. I. du Pont de Nemours Co. of Wilmington, Del. The elastic strands are secured between the non-woven layer 93 and the film layer 95 while in an elastically contractible condition such that contraction of the strands gathers and shortens the distal end 103 of the containment flap 91. As a result, the elastic strands bias the distal end 103 of each flap 91 toward a position spaced from the proximal end 109 of the flap so that the flap extends away from the liner 51 in a generally upright orientation of the flap, especially in the crotch region 27 of the training pants 21, when the pants are fitted on the wearer. It is understood, however, that the containment flaps 91 may each be constructed from a single layer of either non-woven or film material, or they may even be omitted from the training pants 21, without departing from the scope of the invention.

Figure 7:
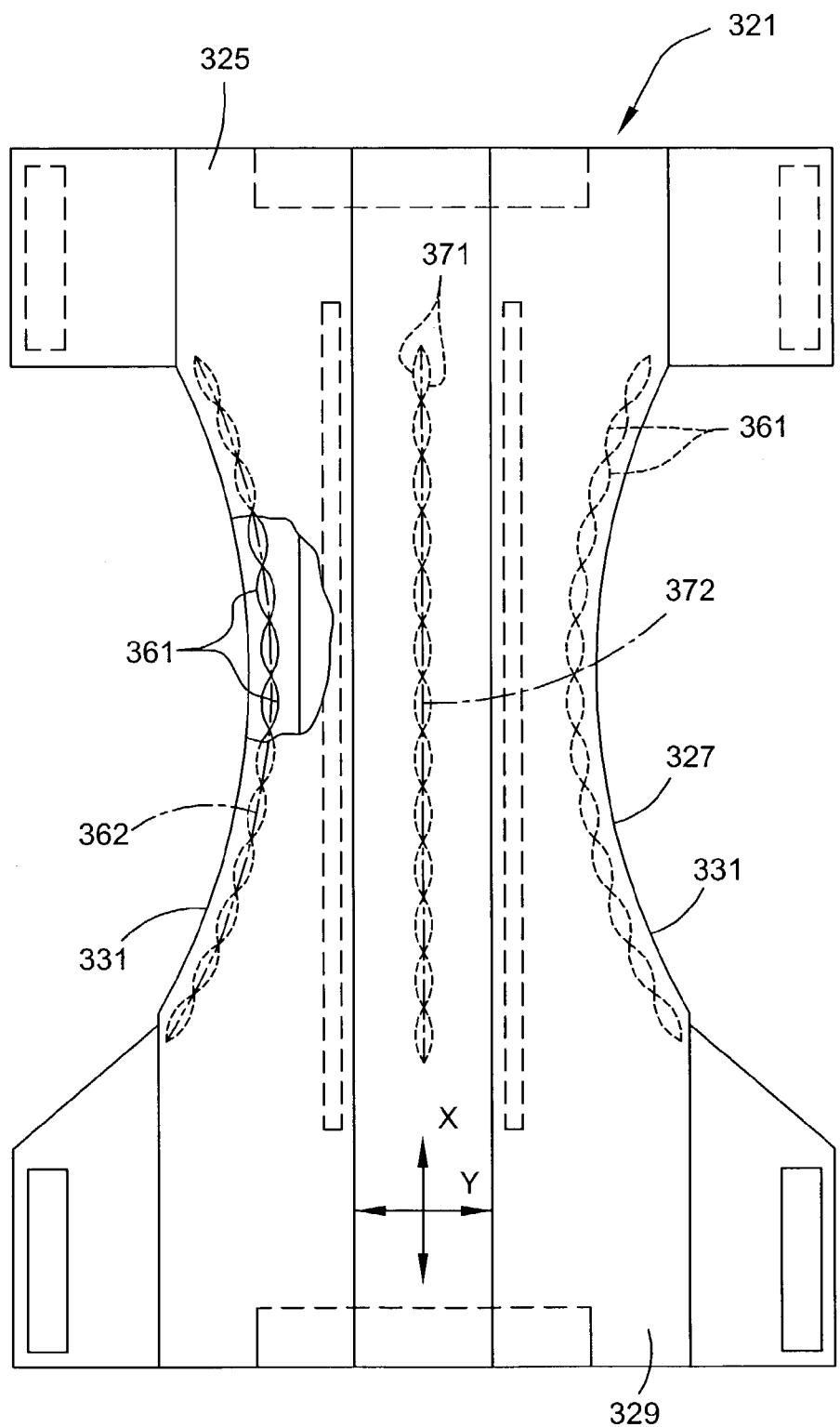
FIG. 7 is a top plan view of training pants similar to FIG. 2 and illustrating central elastic members of the training pants.

FIG. 7 illustrates another pair of training pants 321 which is substantially similar to the training pants 21 of FIG. 2, including having one or more leg elastic members 361 secured therein and extending generally longitudinally along respective elastic axes 362 adjacent the laterally opposite side edges 331 of the pants. The positions of the leg elastic members 361 may or may not vary transversely relative to the respective elastic axes 362 to define wave patterns such as one or more of the wave patterns described previously. The training pants 321 further comprise at least one central elastic member 371 (two are shown in FIG. 7) extending generally longitudinally within the pants, e.g., between the inner and outer layers of the outer cover (not shown in FIG. 7 but substantially the same as the outer cover 49 of the pants 21 of FIG. 2), along respective elastic axes 372 disposed laterally intermediate the leg elastic members. For example, the central elastic members 371 illustrated in FIG. 7 extend generally from the anterior region 325 through the crotch region 327 to the posterior region 329 of the pants 321 intermediate the laterally opposite side edges 331 of the pants, and more particularly intermediate the leg elastic members 361. The elastic axes 372 of the central elastic members 371 are co-linear such that only one common elastic axis is illustrated in the drawing.

The position of each central elastic member 371 varies transversely relative to its respective elastic axis 372 generally in a wave pattern to define a securement path (not shown, but substantially similar to the securement path 63 of FIG. 2A), which as defined previously has a width W. In the illustrated embodiment the elastic axis 372 of each central elastic member 371 extends generally parallel to the longitudinal axis X of the training pants 321. However, it is understood that the elastic axis 372 of each central elastic member 371 may be crooked or otherwise oblique or non-parallel to the longitudinal axis X of the training pants 321 without departing from the scope of this invention. The wave pattern defined by each central elastic member 371 is desirably continuous along at least the segment of its elastic axis 372 which extends through the crotch region 327 of the pants 321, and more desirably along substantially the entire elastic axis as shown in FIG. 7. That is, each central elastic member 371 defines a wave pattern in which the elastic member crosses its elastic axis 372 multiple (e.g., two or more) times as the elastic axis extends within the training pants 321, and more particularly through the crotch region 327 of the training pants.

In the illustrated embodiment, the wave patterns defined by the central elastic members 371 are sinusoidal wave patterns having substantially uniform amplitudes and periods along the respective elastic axes. It is understood, however, that the central elastic members 371 may define one or more of the other wave patterns described previously, or they may define other suitable wave patterns, without departing from the scope of this invention. It is also understood that more than one securement path may be defined by two or more central elastic members 371, for example at least two of the central elastic members may be out of closely spaced relationship with each other and extend longitudinally within the training pants 321 generally laterally intermediate the leg elastic members. It is also contemplated that the wave pattern defined by each central elastic member 371 may have two or more different periods as it extends along different segments of its elastic axis 372. Also, the central elastic members 371 shown in FIG. 7 are generally discrete from the leg elastic members 361. However, it is contemplated that the central elastic members 371 may cross one or more of the leg elastic members 361 as the central elastic members extend along a segment or the entire length of their respective elastic axes and remain within the scope of this invention.

The central elastic members 371 are desirably secured within the pants 321, such as between the outer and inner layers of the outer cover, while in a stretched (e.g., elastically contractible) condition such that retractive forces of the elastic members substantially inhibit expansion of the outer cover of the training pants as the weight of the absorbent body increases following absorption of urine therein. The central elastic members 371 also inhibit sagging of the training pants 321 in the crotch region 327 thereof as the weight of the absorbent body increases to thereby reduce the risk of leakage.

Figure 8:
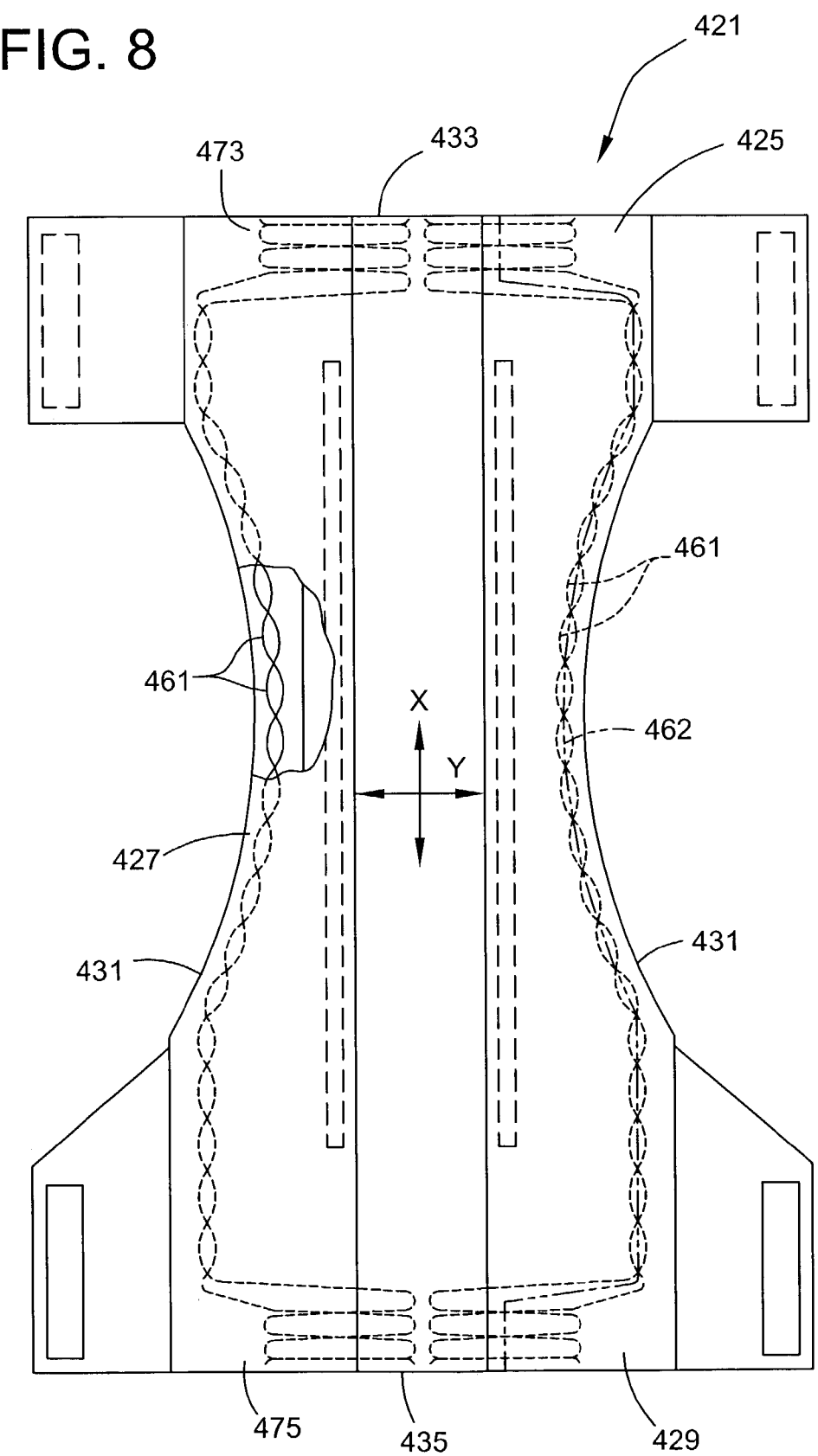
FIG. 8 is a top plan view of training pants similar to FIG. 2 and illustrating another pattern that may be defined by elastic members of the training pants.

Now referring to FIG. 8, another pair of training pants 421 is substantially similar in construction to the training pants 21 of FIG. 2. However, the training pants 421 of FIG. 8 comprises one or more elongate elastic members 461 secured therein and extending longitudinally along respective elastic axes 462 generally adjacent the side edges 431 to longitudinal end or waist margins 473, 475 which are generally adjacent the respective waist edges 433, 435 of the training pants. More particularly, each elastic member 461 extends continuously along its elastic axis 462 generally from one waist margin 473 of the pants 421 at the anterior region 425 thereof through the crotch region 427 generally adjacent a respective one of the side edges 431 of the pants to the waist margin 475 at the posterior region 429 of the pants. Each elastic member 461 is secured within the training pants 421, such as between the inner and outer layers of the outer cover in the manner described previously with respect to FIG. 2.

The position of each elastic member 461 varies transversely relative to its respective elastic axis 462 as it extends along the length of the elastic axis to generally define a wave pattern. For example, each elastic member 461 of the illustrated embodiment defines a periodic wave pattern, e.g., a sinusoidal wave pattern. The amplitude of the wave pattern defined by each elastic member 461 as it extends along its elastic axis 462 generally at the waist margins 473, 475 of the pants 421 is substantially greater than the amplitude of the wave pattern as the elastic member extends along its elastic axis generally through the crotch region 427 of the pants. The frequency of the wave pattern is also greater at the waist margins 473, 475 than in the crotch region 427 of the pants 421. It is contemplated that the elastic members 461 may define any of the wave patterns described previously or it may define other suitable wave patterns without departing from the scope of this invention.

The elastic members 461 extending along their respective elastic axes 462 at the waist margins 473, 475 of the training pants 421 thus extend generally laterally (e.g., in a cross-wise direction) toward the longitudinal axis X of the pants into closely spaced relationship with each other to provide elastic properties similar to that of conventional waist elastics. Extension of the elastic members 461 along their respective elastic axes 462 through the crotch region 427 of the pants 421 provides elastic properties similar to the leg elastic members 61 described previously. Thus it will be seen that the elastic members 461 shown in FIG. 8 unitarily provide elastic retraction at the leg openings (not shown, but similar to the leg openings 47 of FIG. 1) of the training pants 421 and at the waist opening (not shown, but similar to the waist opening 45 of FIG. 1) of the pants. The need for securing a separate elastic component within the training pants 421 at the waist opening is thereby eliminated.

While the elastic composite constructed in accordance with the present invention is shown and described above with particular reference to children's toilet training pants 21, and more specifically to the leg elastics and waist elastics of children's toilet training pants, it is understood that the elastic composite as referred to herein comprises any composite in which an elongate elastic member 61, 361, 461 is applied to a flexible substrate, or between two such substrates, to provide retractive or stretching forces to the substrate in accordance with the present invention.

The substrate may be a film, woven fabric, knit fabric or non-woven fabric. Such fabrics may be of natural or synthetic fibers such as cotton, wool, polyester, nylon, polypropylene, polyethylene, or the like. The film may be of polyethylene, polyester, polyflourocarbons, polyimide, polypropylene, or the like. For example, the flap elastic members 99 of the training pants 21 of FIGS. 1-3 may be secured between the non-woven layer 93 and the film layer 95 of the flaps 91 in accordance with the elastic member patterns shown and described herein. Elastic members may also be secured to the training pants 21 at the front and rear waist edges 33, 35 thereof in accordance with the wave patterns shown and described herein.

The substrate may also be a generally continuous web, such as for forming multiple individual garments such as training pants whereby the web is cut into individual garments after the elastic members are secured to the web. In such an embodiment, the elastic axis of each elastic member may define a pattern which is repeated once for each individual garment to be cut from the web.

It is contemplated that the elastic composite of the present invention may be formed or incorporated in various other garments. For example, other disposable absorbent articles, such as diapers and other infant and child care products, adult incontinence garments and other adult care products, sanitary napkins and other feminine care products and the like, as well as surgical bandages and sponges, may have one or more elastic members secured to one or more layers thereof in accordance with the present invention. Conventional garments such as pants, socks, shirts, hats, coats and the like may also have one or more elastic members secured to one or more layers thereof in accordance with the present invention.

Figure 9:
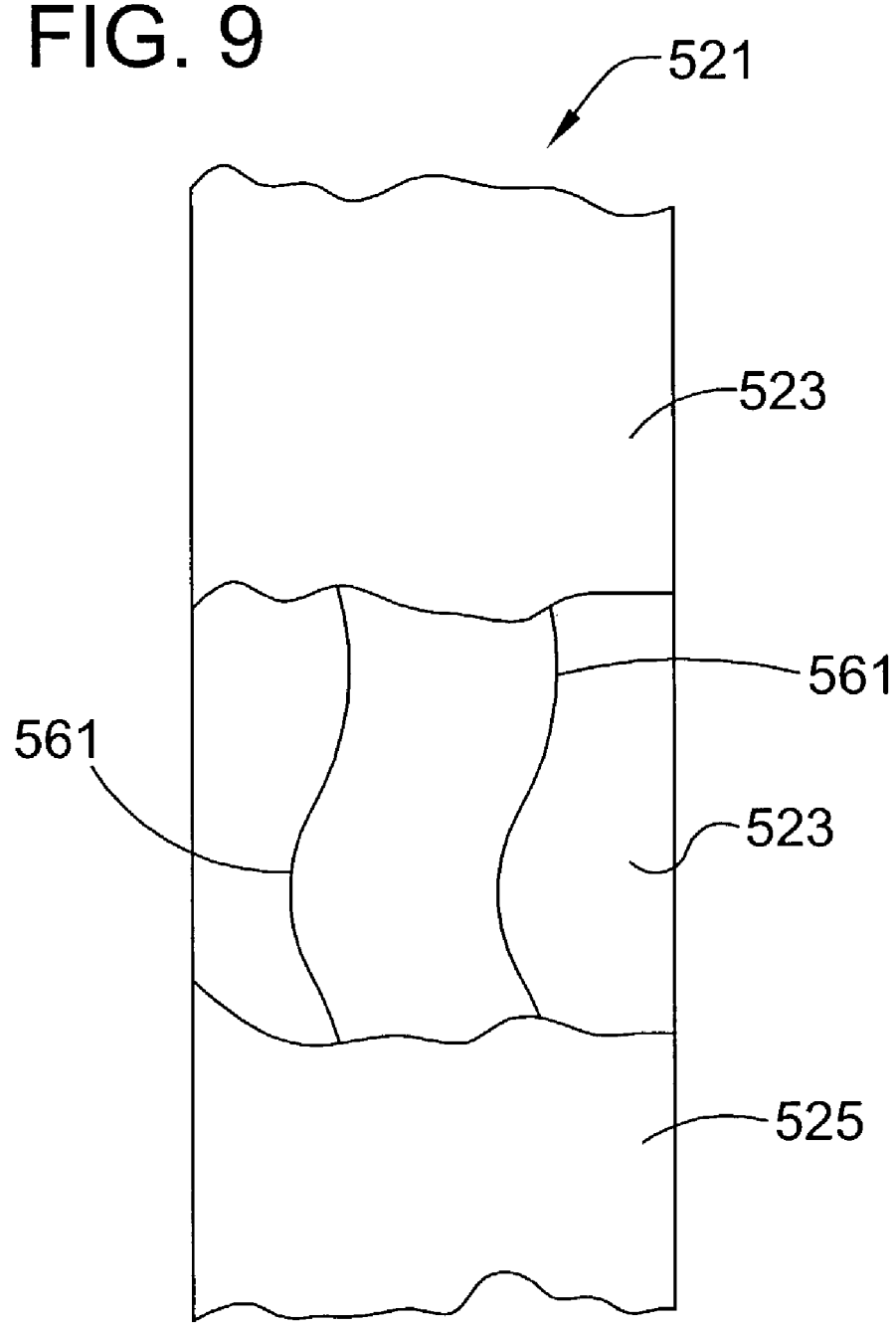
FIG. 9 is a top plan view of another embodiment of an elastic composite of the present invention in the form of an elongate strip, with portions of the composite broken away to reveal various features of the composite.

Alternatively, as shown in FIG. 9, an elastic composite 521 of the present invention may be formed as an elastic strip or ribbon for subsequent securement to an article or garment to provide an elastic component thereto without departing from the scope of this invention. For example, the elastic composite 521 may comprise opposed substrates 523 having one or more elastic members 561 (two are shown in FIG. 9) secured to at least one of the substrates by suitable adhesive. The elastic members 561 may define any of the patterns previously described herein. Also, the substrates 523 may be constructed of any of the materials previously described herein, and may either be of the same material or different materials. It is also contemplated that one of the substrates 561 may be omitted.

The elastic composite 521 shown in FIG. 9 further comprises an additional layer, or facing 525, to which one of the substrates 523 is secured. In one embodiment, the facing 525 can be constructed of either an elastic material or an extensible material such as, for example, a necked material. Methods of making such materials are well known to those skilled in the art and described in U.S. Pat. No. 5,226,992 issued Jul. 13, 1993 to Morman, which is incorporated herein by reference. In other embodiments, the additional facing 525 can be constructed of any of the materials described herein from which the substrates 523 can be constructed.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An elastic composite comprising:
a substrate having a longitudinal axis; and
an elongate elastic member secured to the substrate and extending generally longitudinally of the substrate along an elastic axis of said elastic member between a first location on the substrate and a second location on the substrate spaced longitudinally from the first location, at least a portion of the elastic axis being generally non-parallel to the longitudinal axis of the substrate, the elastic member crossing its elastic axis at least twice as it extends along said elastic axis, said elastic member crossing itself at least once as it extends along said elastic axis.

2. An elastic composite as set forth in claim 1 wherein the elastic member defines a continuous series of loops.

3. An elastic composite as set forth in claim 2 wherein each loop defines a closed portion having a generally tear-drop shape.

4. An elastic composite as set forth in claim 1 wherein the elastic composite is a disposable absorbent article comprising a liner adapted, for contiguous relation with the wearer's skin, an outer cover and an absorbent body between the liner and the outer cover for absorbing liquid body waste, said elastic member being secured within the article.

5. An elastic composite as set forth in claim 1 further comprising a facing, the substrate to which the elastic member is secured being secured to the facing, said facing being constructed of at least one of an elastic material and an extensible material.

* * * * *